(12) United States Patent
Chen et al.

(10) Patent No.: US 7,256,284 B2
(45) Date of Patent: Aug. 14, 2007

(54) INHIBITORY OLIGONUCLEOTIDES TARGETED TO BCL-2

(75) Inventors: Zhidong Chen, Salt Lake City, UT (US); Duane E. Ruffner, Salt Lake City, UT (US); Ramesh Prakash, Salt Lake City, UT (US); Richard Koehn, Salt Lake City, UT (US)

(73) Assignee: Genta Incorporated, Berkeley Heights, NJ (US)

( * ) Notice: Subject to any disclaimer, the term of this patent is extended or adjusted under 35 U.S.C. 154(b) by 347 days.

(21) Appl. No.: 10/714,310

(22) Filed: Nov. 14, 2003

(65) Prior Publication Data

US 2004/0152654 A1 Aug. 5, 2004

Related U.S. Application Data

(60) Provisional application No. 60/426,269, filed on Nov. 14, 2002.

(51) Int. Cl.
*C07H 21/02* (2006.01)
*C07H 21/04* (2006.01)

(52) U.S. Cl. .................. 536/24.5; 536/23.1; 536/24.3; 536/24.33

(58) Field of Classification Search ............... 536/24.1, 536/24.3, 24.33, 24.5
See application file for complete search history.

(56) References Cited

U.S. PATENT DOCUMENTS

| | | | |
|---|---|---|---|
| 5,912,147 A * | 6/1999 | Stoler et al. | 435/91.2 |
| 6,040,181 A | 3/2000 | Reed | |
| 6,043,031 A * | 3/2000 | Koster et al. | 435/6 |
| 6,310,047 B1 | 10/2001 | Farrell et al. | |

FOREIGN PATENT DOCUMENTS

| | | |
|---|---|---|
| WO | WO 99/50457 | 10/1999 |
| WO | WO 00/61810 | 10/2000 |
| WO | WO 01/13914 | 3/2001 |
| WO | WO 01/59156 | 8/2001 |
| WO | WO 0160998 | 8/2001 |
| WO | WO 02/17852 | 3/2002 |
| WO | WO 02/057480 | 7/2002 |

OTHER PUBLICATIONS

International Search Report for PCT/US03/36614.
Ziegler, Annemarie, et al. "Induction of apoptosis in small cell lung cancer cells by antisense oligodeoxynucleotide targeting the Bcl-2 coding sequence" Journal for National Cancer Institute Jul. 16, 1997 89:14, p. 1027-1036.
Woodle, M. C. et al, "Oligonucleotide pharmacology and formulation: G3139 anti-bcl2 phosphorothioate in stealth liposomes and gel implants" Nucleosides & Nucleotides, 1997 16:(7-9) p. 1731-1734.
Supplementary Partial European Search Report for EP 03786757 dated Oct. 4, 2006.

* cited by examiner

*Primary Examiner*—Sean McGarry
*Assistant Examiner*—Terra C. Gibbs
(74) *Attorney, Agent, or Firm*—Kenyon & Kenyon LLP (57) ABSTRACT

Inhibitory oligonucleotides are disclosed which are targeted to three specific target regions and subsequences of the target regions found on nucleic acids encoding Bcl-2. These inhibitory oligonucleotides are generally of from about 8 to about 50 nucleotides in length. Specific preferred oligonucleotides are disclosed. The oligonucleotides of the invention may be incorporated into compositions such as pharmaceutical compositions, and may be used in methods for inhibiting the expression of Bcl-2 in a cell or tissue, methods for treating conditions susceptible to modulation of Bcl-2 expression in an organism, and methods for detecting nucleic acid encoding BCL-2.

8 Claims, 3 Drawing Sheets

SEQUENCE LISTING

```
<160> NUMBER OF SEQ ID NOS: 38

<210> SEQ ID NO 1
<211> LENGTH: 14
<212> TYPE: DNA
<213> ORGANISM: Homo sapiens

<400> SEQUENCE: 1
agcgtgcgcc atcc                                                      14

<210> SEQ ID NO 2
<211> LENGTH: 14
<212> TYPE: DNA
<213> ORGANISM: Homo sapiens

<400> SEQUENCE: 2
cgccatcctt ccca                                                      14

<210> SEQ ID NO 3
<211> LENGTH: 14
<212> TYPE: DNA
<213> ORGANISM: Homo sapiens

<400> SEQUENCE: 3
atccttccca gagg                                                      14

<210> SEQ ID NO 4
<211> LENGTH: 14
<212> TYPE: DNA
<213> ORGANISM: Homo sapiens

<400> SEQUENCE: 4
cccagaggaa aagc                                                      14

<210> SEQ ID NO 5
<211> LENGTH: 18
<212> TYPE: DNA
<213> ORGANISM: Homo sapiens

<400> SEQUENCE: 5
ccttcccaga ggaaaagc                                                  18

<210> SEQ ID NO 6
<211> LENGTH: 14
<212> TYPE: DNA
<213> ORGANISM: Homo sapiens

<400> SEQUENCE: 6
ccttcccaga ggaa                                                      14
```

```
<210> SEQ ID NO 7
<211> LENGTH: 14
<212> TYPE: DNA
<213> ORGANISM: Homo sapiens

<400> SEQUENCE: 7
catccttccc agag                                                      14

<210> SEQ ID NO 8
<211> LENGTH: 14
<212> TYPE: DNA
<213> ORGANISM: Homo sapiens

<400> SEQUENCE: 8
gggagaagtc gtcg                                                      14

<210> SEQ ID NO 9
<211> LENGTH: 14
<212> TYPE: DNA
<213> ORGANISM: Homo sapiens

<400> SEQUENCE: 9
cggcttggcg gagg                                                      14

<210> SEQ ID NO 10
<211> LENGTH: 14
<212> TYPE: DNA
<213> ORGANISM: Homo sapiens

<400> SEQUENCE: 10
ccccgcgcgg tgaa                                                      14

<210> SEQ ID NO 11
<211> LENGTH: 14
<212> TYPE: DNA
<213> ORGANISM: Homo sapiens

<400> SEQUENCE: 11
ccgcgcggtg aagg                                                      14

<210> SEQ ID NO 12
<211> LENGTH: 14
<212> TYPE: DNA
<213> ORGANISM: Homo sapiens

<400> SEQUENCE: 12
cgcgcggtga aggg                                                      14

<210> SEQ ID NO 13
<211> LENGTH: 13
<212> TYPE: DNA
<213> ORGANISM: Homo sapiens

<400> SEQUENCE: 13
gcgcggtgaa ggg                                                       13

<210> SEQ ID NO 14
<211> LENGTH: 14
<212> TYPE: DNA
<213> ORGANISM: Homo sapiens

<400> SEQUENCE: 14
```

-continued

| | |
|---|---|
| tcccagagga aaag | 14 |

<210> SEQ ID NO 15
<211> LENGTH: 30
<212> TYPE: DNA
<213> ORGANISM: Homo sapiens

<400> SEQUENCE: 15

| | |
|---|---|
| gcttttcctc tgggaaggat ggcgcacgct | 30 |

<210> SEQ ID NO 16
<211> LENGTH: 14
<212> TYPE: DNA
<213> ORGANISM: Homo sapiens

<400> SEQUENCE: 16

| | |
|---|---|
| cgacgacttc tccc | 14 |

<210> SEQ ID NO 17
<211> LENGTH: 17
<212> TYPE: DNA
<213> ORGANISM: Homo sapiens

<400> SEQUENCE: 17

| | |
|---|---|
| cccttcaccg cgcgggg | 17 |

<210> SEQ ID NO 18
<211> LENGTH: 931
<212> TYPE: DNA
<213> ORGANISM: Homo sapiens

<400> SEQUENCE: 18

| | |
|---|---|
| gctggggcga gaggtgccgt tggcccccgt tgcttttcct ctgggaagga tggcgcacgc | 60 |
| tgggagaacg gggtacgaca accgggagat agtgatgaag tacatccatt ataagctgtc | 120 |
| gcagagggc tacgagtggg atgcgggaga tgtgggcgcc gcgcccccgg gggccgcccc | 180 |
| cgcaccgggc atcttctcct cccagcccgg gcacacgccc catccagccg catcccgcga | 240 |
| cccggtcgcc aggacctcgc cgctgcagac cccggctgcc cccggcgccg ccgcggggcc | 300 |
| tgcgctcagc ccggtgccac ctgtggtcca cctggccctc cgccaagccg gcgacgactt | 360 |
| ctcccgccgc taccgcggcg acttcgccga gatgtccagc cagctgcacc tgacgccctt | 420 |
| caccgcgcgg ggacgctttg ccacggtggt ggaggagctc ttcagggacg gggtgaactg | 480 |
| ggggaggatt gtggccttct ttgagttcgg tggggtcatg tgtgtggaga gcgtcaaccg | 540 |
| ggagatgtcg cccctggtgg acaacatcgc cctgtggatg actgagtacc tgaaccggca | 600 |
| cctgcacacc tggatccagg ataacggagg ctgggatgcc tttgtggaac tgtacggccc | 660 |
| cagcatgcgg cctctgtttg atttctcctg gctgtctctg aagactctgc tcagtttggc | 720 |
| cctggtggga gcttgcatca ccctgggtgc ctatctgagc cacaagtgaa gtcaacatgc | 780 |
| ctgccccaaa caaatatgca aaaggttcac taaagcagta gaaataatat gcattgtcag | 840 |
| tgatgtacca tgaaacaaag ctgcaggctg tttaagaaaa aataacacac atataaacat | 900 |
| cacacacaca gacagacaca cacacacaca a | 931 |

<210> SEQ ID NO 19
<211> LENGTH: 40
<212> TYPE: DNA
<213> ORGANISM: Homo sapiens

<400> SEQUENCE: 19

```
gcttttcctc tgggaaggat ggcgcacgct gggagaacgg              40
```

<210> SEQ ID NO 20
<211> LENGTH: 62
<212> TYPE: DNA
<213> ORGANISM: Homo sapiens

<400> SEQUENCE: 20

```
cctccgccaa gccggcgacg acttctcccg ccgctaccgc ggcgacttcg ccgagatgtc    60
ca                                                                  62
```

<210> SEQ ID NO 21
<211> LENGTH: 23
<212> TYPE: DNA
<213> ORGANISM: Homo sapiens

<400> SEQUENCE: 21

```
gacgcccttc accgcgcggg gac                               23
```

<210> SEQ ID NO 22
<211> LENGTH: 14
<212> TYPE: DNA
<213> ORGANISM: Homo sapiens

<400> SEQUENCE: 22

```
gccatccttc ccag                                         14
```

<210> SEQ ID NO 23
<211> LENGTH: 14
<212> TYPE: DNA
<213> ORGANISM: Homo sapiens

<400> SEQUENCE: 23

```
cgtgcgccat cctt                                         14
```

<210> SEQ ID NO 24
<211> LENGTH: 14
<212> TYPE: DNA
<213> ORGANISM: Homo sapiens

<400> SEQUENCE: 24

```
gcgtgcgcca tcct                                         14
```

<210> SEQ ID NO 25
<211> LENGTH: 14
<212> TYPE: DNA
<213> ORGANISM: Homo sapiens

<400> SEQUENCE: 25

```
ccgttctccc agcg                                         14
```

<210> SEQ ID NO 26
<211> LENGTH: 14
<212> TYPE: DNA
<213> ORGANISM: Homo sapiens

<400> SEQUENCE: 26

```
gcggtagcgg cggg                                         14
```

<210> SEQ ID NO 27
<211> LENGTH: 14
<212> TYPE: DNA

```
<213> ORGANISM: Homo sapiens

<400> SEQUENCE: 27
cgccgcggta gcgg                                                       14

<210> SEQ ID NO 28
<211> LENGTH: 14
<212> TYPE: DNA
<213> ORGANISM: Homo sapiens

<400> SEQUENCE: 28
ggacatctcg gcga                                                       14

<210> SEQ ID NO 29
<211> LENGTH: 20
<212> TYPE: DNA
<213> ORGANISM: Homo sapiens

<400> SEQUENCE: 29
agaagtcgtc gccggcttgg                                                 20

<210> SEQ ID NO 30
<211> LENGTH: 20
<212> TYPE: DNA
<213> ORGANISM: Homo sapiens

<400> SEQUENCE: 30
tggacatctc ggcgaagtcg                                                 20

<210> SEQ ID NO 31
<211> LENGTH: 20
<212> TYPE: DNA
<213> ORGANISM: Homo sapiens

<400> SEQUENCE: 31
cccgcgcggt gaagggcgtc                                                 20

<210> SEQ ID NO 32
<211> LENGTH: 18
<212> TYPE: DNA
<213> ORGANISM: Homo sapiens

<400> SEQUENCE: 32
ccccgcgcgg tgaagggc                                                   18

<210> SEQ ID NO 33
<211> LENGTH: 14
<212> TYPE: DNA
<213> ORGANISM: Homo sapiens

<400> SEQUENCE: 33
cccgcgcggt gaag                                                       14

<210> SEQ ID NO 34
<211> LENGTH: 14
<212> TYPE: DNA
<213> ORGANISM: Homo sapiens

<400> SEQUENCE: 34
gtccccgcgc ggtg                                                       14

<210> SEQ ID NO 35
<211> LENGTH: 931
```

-continued

<212> TYPE: DNA
<213> ORGANISM: Homo sapiens

<400> SEQUENCE: 35

| gctggggcga | gaggtgccgt | tggcccccgt | tacttttcct | ctgggaaata | tggcgcacgc | 60 |
| tgggagaaca | gggtacgaca | accgggagat | agtgatgaag | tacatccatt | ataagctgtc | 120 |
| gcagaggggc | tacgagtggg | atgcgggaga | tgtgggcgcc | cgcgccccgg | gggccgcccc | 180 |
| cgcgccgggc | atcttctcct | cgcagcccgg | gcacacgccc | catacagccg | catcccggga | 240 |
| cccggtcgcc | aggacctcgc | cgctgcagac | cccggctgcc | cccggcgccg | ccgcggggcc | 300 |
| tgcgctcagc | ccggtgccac | ctgtggtcca | cctgaccctc | cgccaggccg | gcgacgactt | 360 |
| ctcccgccgc | taccgccgcg | acttcgccga | gatgtccagg | cagctgcacc | tgacgccctt | 420 |
| caccgcgcgg | ggacgctttg | ccacggtggt | ggaggagctc | ttcagggacg | gggtgaactg | 480 |
| ggggaggatt | gtggccttct | ttgagttcgg | tggggtcatg | tgtgtggaga | gcgtcaaccg | 540 |
| ggagatgtcg | cccctggtgg | acaacatcgc | cctgtggatg | actgagtacc | tgaaccggca | 600 |
| cctgcacacc | tggatccagg | ataacggagg | ctgggatgcc | tttgtggaac | tgtacgcccc | 660 |
| cagcatgcgg | cctctgtttg | atttctcctg | gctgtctctg | aagactctgc | tcagtttggc | 720 |
| cctggtggga | gcttgcatca | ccctgggtgc | ctatctgggc | acaagtgaa | gtcaacatgc | 780 |
| ctgccccaaa | caaatatgca | aaaggttcac | taaagcagta | gaaataatat | gcattgtcag | 840 |
| tgatgttcca | tgaaacaaag | ctgcaggctg | tttaagaaaa | aataacacac | atataaacat | 900 |
| cacacacaca | gacagacaca | cacacacaca | a | | | 931 |

<210> SEQ ID NO 36
<211> LENGTH: 40
<212> TYPE: DNA
<213> ORGANISM: Homo sapiens

<400> SEQUENCE: 36

| acttttcctc | tgggaaatat | ggcgcacgct | gggagaacag | 40 |

<210> SEQ ID NO 37
<211> LENGTH: 62
<212> TYPE: DNA
<213> ORGANISM: Homo sapiens

<400> SEQUENCE: 37

| cctccgccag | gccggcgacg | acttctcccg | ccgctaccgc | cgcgacttcg | ccgagatgtc | 60 |
| ca | | | | | | 62 |

<210> SEQ ID NO 38
<211> LENGTH: 480
<212> TYPE: DNA
<213> ORGANISM: Homo sapiens

<400> SEQUENCE: 38

| gttggccccc | gttgcttttc | tctctgggaag | gatggcgcac | gctgggagaa | cggggtacga | 60 |
| caaccgggag | atagtgatga | agtacatcca | ttataagctg | tcgcagaggg | gctacgagtg | 120 |
| ggatgcggga | gatgtgggcg | ccgcgccccc | ggggccgcc | cccgcaccgg | gcatcttctc | 180 |
| ctcccagccc | gggcacacgc | cccatccagc | cgcatcccgc | gacccggtcg | ccaggacctc | 240 |
| gccgctgcag | accccggctg | cccccggcgc | gccgcgggg | cctgcgctca | gcccggtgcc | 300 |
| acctgtggtc | cacctggccc | tccgccaagc | cggcgacgac | ttctcccgcc | gctaccgcgg | 360 |

```
                                               -continued cgacttcgcc gagatgtcca gccagctgca cctgacgccc ttcaccgcgc ggggacgctt      420
tgccacggtg gtggaggagc tcttcaggga cggggtgaac tggggagga ttgtggcctt       480
```

INHIBITORY OLIGONUCLEOTIDES TARGETED TO BCL-2

CROSS-REFERENCE TO RELATED APPLICATIONS

This application claims the benefit of U.S. Provisional Application No. 60/426,269, filed Nov. 14, 2002.

BACKGROUND OF THE INVENTION

1. Field of the Invention

The present invention relates generally to agents and nucleic acid targets for regulating gene expression. More specifically, the present invention relates to compounds, compositions, and methods for regulation of the expression of nucleic acids encoding Bcl-2.

2. Technical Background

The genetic blueprint of mankind is written and stored in the chromosomes found in the nuclei of somatic cells. These chromosomes are each made up of a single molecule of DNA. DNA is a double-stranded polymer compound whose strands are chains of the nucleotide subunits adenine, thymine, cytosine, and guanine. These chains are held to each other by hydrogen bonds formed between complementary nucleotides on the chains. Adenine (A) forms hydrogen bonds with thymine (T); and guanine (G) forms hydrogen bonds with cytosine (C). Contiguous sets of three of these nucleobases in the nucleotide strands code for individual amino acids. Together, the nucleotide chains of DNA code for all of the various proteins needed to build, maintain, and fuel the human body.

Proteins are translated from transcribed copies of DNA called messenger RNA. Messenger RNA is made when DNA partially unwinds, allowing the sequence of the DNA to be copied and transcribed by cellular machinery. Messenger RNA is made of similar components as DNA, with the substitution of uracil for thymine and the substitution of ribose for deoxyribose in all nucleotides. Once the transcription of a messenger RNA is completed, it is transported from the nucleus to the cytosol. There, the mRNA is engaged by the enzymes that are the protein-manufacturing machinery of the cell. The enzymes and other associated molecules making up this machinery bind to the mRNA and begin to interpret the code of the messenger RNA. As they do so, they also assemble and bind the amino acids encoded into chains to produce the protein coded for by the original DNA.

Illnesses and disease states such as some cancers have been linked to the over-, under-, or mis-production of specific proteins. In some of these cases, a defect present in the gene causes the production of messenger RNAs that code for a nonfunctional or inefficient protein. Additionally, some diseases may be controlled by increasing or decreasing the normal production of a protein. Specifically, it is thought that in some cancers, if the gene coding for a specific protein could be regulated, the cancer would abate, or would become more susceptible to treatment. As a result of this, much research has been conducted to find a method of modulating the activity of a gene. In one specific study, it was determined that down-regulation of Bcl-2 production in prostate cancer cells inhibited their growth and rendered them susceptible to adriamycin-induced apoptosis. Shi et al., *Cancer Biother. Radiopharm.*, 16(5):421-9 (October 2001).

One technology used for regulating the expression of a gene is antisense technology. Antisense technology controls the production of a protein by binding a molecule to the nucleic acid coding for the protein. Generally this molecule is a short length of DNA or RNA commonly referred to as an antisense oligonucleotide. These oligonucleotides are complementary to a segment of the nucleic acid. In use, these antisense oligonucleotides are administered to a cell or tissue desired to be treated. The oligonucleotides are taken into the cell where they associate with and bind to a region of the nucleic acid encoding the protein to which they are complementary. This binding prevents normal interaction of the nucleic acid with cellular machinery such as RNA translation enzymes or induces the degradation of the message RNA. This inhibits or prevents proper translation of the message RNA.

Antisense is regarded by many as a powerful technology since the antisense oligonucleotides used may be carefully targeted to specific regions on the nucleic acids, thus preventing interaction of the oligonucleotides with other molecules not desired to be inhibited or activated. These specific regions of the selected nucleic acids are often referred to as target sequences. Because antisense oligonucleotides may be so carefully targeted to these target sequences, antisense oligonucleotides may be used to provide compositions, such as drugs, that have near-absolute specificity, high efficacy, low toxicity, and few side effects.

These benefits are overshadowed, however, by the difficulty involved in locating effective antisense oligonucleotides for use with a gene. Despite the fact that generally there are a large number of potential oligonucleotides available for each individual gene, different antisense oligonucleotides have different effects on gene expression. This has been shown to be due at least in part to the final folded structure of the nucleic acid which may block access to some regions of the nucleic acid sequence, thus rendering some oligonucleotides ineffective. Further, the work of characterizing effective sites must be repeated for each individual gene desired to be targeted. This process is generally a long and expensive one. Many disease states, including cancer, stand to benefit from successful antisense therapies, but oligonucleotides useful with specific genes are elusive.

Bcl-2 is an inner mitochondrial membrane protein that has been shown to block apoptotic cell death in some specific cell types. The expression of Bcl-2 has been shown to be involved in apoptosis in the thymus (Kanavaros et al., *Histol. Histopathol.* 16(4):1005-12 (October 2001). Bcl-2 has also been shown to play a role in prostatic cancers, and has been specifically linked to aggressive tumors common in specific racial groups. Shi et al., *Cancer Biother. Radiopharm.*, 16(5):421-9 (October 2001); Slothower, *Study Suggests Bcl-2 Gene as a Cause for Aggressive Prostate Cancer in African American Men, U.C. Davis Med. Ctr.*, (May 1998). As briefly noted above, a study in which Bcl-2 production was down-regulated in prostate cancer cells showed inhibition of cell growth and increased sensitivity to treatments designed to induce apoptosis. Shi et al., *Biother. Radiopharm.*, 16(5):421-9 (October 2001).

Accordingly, it would be an advancement in the art to provide inhibitory oligonucleotide compounds configured to bind to, and consequently, to modulate the activity of nucleic acids encoding proteins which play a role in diseases such as cancer. It would be a further advancement to provide effective target sites for Bcl-2 gene regulation. It would be an advancement in the art to provide oligonucleotides complementary to effective antisense target regions of a nucleic acid encoding Bcl-2. It would be a further benefit in the art to provide compositions such as medications, including such oligonucleotides. Finally, it would be an improvement in the art to provide methods of using such oligonucleotides and compositions.

Such oligonucleotides, target regions, compositions including such oligonucleotides, and methods of their use are disclosed herein.

BRIEF SUMMARY OF THE INVENTION

The present invention is directed to oligonucleotides that are targeted to nucleic acids which encode Bcl-2. The compounds are designed to be complementary to at least a part of a target region of a nucleic acid encoding Bcl-2, and as a result, to modulate the expression of Bcl-2.

The invention first encompasses compounds such as oligonucleotides configured to hybridize with at least a portion of an oligonucleotide encoding Bcl-2. One such oligonucleotide encoding Bcl-2 is the oligonucleotide of SEQ ID NO: 18. A sequence variant of a Bcl-2 cDNA is shown in SEQ ID NO: 35. Some of these compounds are oligonucleotides of between about 8 and about 30 nucleobases in length having at least 8 contiguous nucleobases complementary to at least a portion of SEQ ID NO: 18. As used herein, the term "nucleobase" refers to adenine (A), cytosine (C), guanine (G), thymine (T) and uracil (U); their post-replicationally or post-transcriptionally modified derivatives; and other bases suitable for inclusion in a nucleic acid. Inhibitory oligonucleotides of the invention are presented in the attached Sequence Listing as DNA sequences for convenience. It is to be understood, however, that the corresponding RNA inhibitory sequences, routinely obtained by substituting "U" for "T" in the sequences set forth in the Sequence Listing, are included in the invention.

In specific embodiments, the oligonucleotides of the invention include at least about 8 contiguous nucleotides complementary to at least a portion of SEQ ID NO: 19 or SEQ ID NO: 36, preferably complementary to at least a portion of SEQ ID NO: 15. Some such oligonucleotides have a sequence selected from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 14, SEQ ID NO: 22, SEQ ID NO: 23, SEQ ID NO:24 and SEQ ID NO:25.

In other embodiments, the oligonucleotides of the invention include at least about 8 contiguous nucleotides complementary to at least a portion of SEQ ID NO: 20 or SEQ ID NO: 37, preferably complementary to at least a portion of SEQ ID NO: 16. Some such oligonucleotides have a sequence selected from the group comprising SEQ ID NO: 8, SEQ ID NO: 9, SEQ ID NO: 26, SEQ ID NO: 27, SEQ ID NO: 28, SEQ ID NO: 29 and SEQ ID NO:30.

In other embodiments, the oligonucleotides of the invention include at least about 8 contiguous nucleotides complementary to at least a portion of SEQ ID NO: 21, preferably complementary to at least a portion of SEQ ID NO: 17. Some such oligonucleotides have a sequence selected from the group comprising SEQ ID NO: 10, SEQ ID NO: 11, SEQ ID NO: 12, SEQ ID NO: 13, SEQ ID NO: 31, SEQ ID NO: 32, SEQ ID NO: 33 and SEQ ID NO: 34.

The oligonucleotides of the invention may include features or components such as modified internucleotide linkages, modified sugar moieties, and modified nucleobases. The oligonucleotides may also contain nucleotides from DNA or RNA.

The invention further includes compositions such as pharmaceuticals including the oligonucleotide compounds disclosed above that are targeted to any of the target regions of the invention found in SEQ ID NO: 18 or SEQ ID NO: 35, including the regions of SEQ ID NO: 15, SEQ ID NO: 16, SEQ ID NO: 17, SEQ ID NO: 19, SEQ ID NO: 20, SEQ ID NO: 21, SEQ ID NO: 36 and SEQ ID NO: 37. Such compositions may include additional components such as pharmaceutically-acceptable carriers, diluents or adjuvants.

The invention also includes methods of inhibiting the expression of Bcl-2 in a cell or tissue. Such methods include the step of contacting the cell or tissue with a composition made with the oligonucleotides of the invention. Such oligonucleotides may include compounds comprising a segment of from about 8 to about 30 nucleobases in length of a sequence chosen from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 36 and SEQ ID NO: 37.

BRIEF DESCRIPTION OF THE DRAWINGS

A more particular description of the invention briefly described above will be rendered by reference to specific embodiments thereof which are illustrated in the appended drawings. These drawings depict only typical embodiments of the invention and are not therefore to be considered to be limiting of its scope. The invention will be described and explained with additional specificity and detail through the use of the accompanying drawings and detailed description, in which.

DETAILED DESCRIPTION

The practice of the present invention will employ, unless otherwise indicated, conventional methods of virology, microbiology, molecular biology, and recombinant DNA techniques within the skill of the art. Such techniques are fully explained in the literature. See, e.g., Sambrook, et al., *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijessen, ed.); *Fundamental Virology*, 2nd Edition, vol. I & II (B. N. Fields & D. M. Knipe, eds.).

All publications, patents and patent applications cited herein, whether supra or infra, are hereby incorporated by reference in their entirety. As used in this specification and the appended claims, the singular forms "a," "and," and "the" include plural references unless the content clearly dictates otherwise.

The present invention relates to oligomeric compounds for modulating the function of nucleic acid molecules encoding Bcl-2. More specifically, the invention relates to oligomeric compounds such as inhibitory oligonucleotides that are configured to interact with nucleic acids encoding Bcl-2. The invention further includes compositions comprising such oligonucleotides, including pharmaceutical compounds, and methods for their use. The invention additionally includes methods of treating diseases that respond to the modulation of Bcl-2 such as several cancers.

1. Definitions

The following terms will be used in describing the compounds and methods of the instant invention. They are intended to be defined as indicated hereafter.

As used herein, the terms "oligonucleotide" and "nucleic acid" denote polynucleotides—polymers of nucleotides. Further, as used herein, the terms "target nucleic acid" and "nucleic acid encoding Bcl-2" include polynucleotides having at least a portion of the sense or antisense code for Bcl-2. DNA encoding Bcl-2 is thus included, as is RNA such as pre-mRNA and mRNA, cDNA, and hybrid nucleic acids such as artificial sequences having at least a portion of the sequence of Bcl-2. Herein, the terms "nucleic acid," "target nucleic acid," and "nucleic acids encoding Bcl-2" also include sequences having any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl)uracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs.

In the context of this invention, the term "oligonucleotides" refers to an oligomer or polymer of ribonucleic acid (RNA) or deoxyribonucleic acid (DNA) or analogs thereof. This term includes oligonucleotides composed of naturally-occurring nucleobases, sugars and internucleotide (or "backbone") linkages, as well as oligonucleotides having non-naturally occurring portions with similar function.

Herein, the term "inhibitory oligonucleotide" denotes an oligonucleotide having a sequence that enables the oligonucleotide to interact with a selected portion of a nucleic acid. This interaction is often sufficient to result in the disruption of the function of the nucleic acid. The oligonucleotides of the invention may be either RNA or DNA and have a sequence that is substantially complementary to at least a segment of the selected portion of the nucleic acid. As such, the oligonucleotide may have a substantially sense sequence or a substantially antisense sequence. Such oligonucleotides may disrupt the function of the nucleic acid by specifically hybridizing with it. Some such oligonucleotides may specifically hybridize to the selected portion of the nucleic acid. Additionally, the inhibitory oligonucleotide may have a sequence that is substantially identical to that of the selected portion of the nucleic acid.

The term "antisense oligonucleotide" is used herein to denote an oligonucleotide which is complementary to, and thus has the capacity to specifically hybridize with, a nucleic acid. This is especially used herein to refer to oligonucleotides whose binding modulates the normal activity or function of the target nucleic acid. The modulation of nucleic acid activity caused by such oligonucleotides is broadly termed "antisense" technology. Antisense oligonucleotides may be either RNA or DNA.

The inhibitory oligonucleotides of the present invention include antisense oligonucleotides. The antisense oligonucleotides of the invention may be equal in size to the entire target sequence to which they are targeted. Alternatively, such oligonucleotides may be from about 8 to about 50 nucleobases in length (i.e. from about 8 to about 50 linked nucleosides). Still further, the oligonucleotide compounds may be antisense oligonucleotides of from about 10 to about 30 nucleobases in length. The antisense oligonucleotide compounds of the invention may be either RNA or DNA and include without limitation ribozymes, external guide sequences (EGS), oligozymes, other short catalytic RNAs and other catalytic oligonucleotides, or other short RNAs such as siRNA, miRNA, and shRNA, etc., which are configured to hybridize to the target nucleic acid and modulate its expression or integrity.

The term "complementary," as used herein, refers to the capacity of two nucleotides to pair precisely with each other. This is often termed "Watson-Crick pairing." This term may also be used to refer to oligonucleotides which exhibit the ability of pairing precisely with each other. For example, if the nucleotides located at a certain position on two oligonucleotides are capable of hydrogen bonding, then the oligonucleotides are considered to be complementary to each other at that position. The oligonucleotides and the DNA or RNA themselves are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise paring such that stable and specific binding may occur between the oligonucleotides and the DNA or RNA target.

It is understood in the art that the sequence of an inhibitory oligonucleotide compound need not be 100 percent complementary to that of its target nucleic acid to be specifically hybridizable. An inhibitory oligonucleotide compound is specifically hybridizable when binding of the compound to the target DNA or RNA molecule interferes with the normal function of the target DNA or RNA. A sufficient degree of complementarity prevents non-specific binding of the inhibitory oligonucleotide compound to non-target sequences under conditions in which specific binding is desired, i.e. under physiological conditions in the case of in vivo assays or therapeutic treatment, and in the case of in vitro assays, under conditions in which the assays are performed.

As is known in the art, a nucleoside is a combination of a base and a sugar. The base portion of the nucleoside is normally a heterocyclic base. The two most common classes of heterocyclic bases are purines and pyrimidines.

Nucleotides are nucleosides that additionally include a phosphate group linked to the sugar portion of the nucleoside. For those nucleosides that include a pentafuranosyl sugar, the phosphate group can be linked to either the 2', 3', or 5' hydroxyl moiety of the sugar. In forming oligonucleotides, the phosphate groups link adjacent nucleosides to one another to a form a linear polymer. The ends of such linear polymers can also be joined, thus forming a circular structure. Within the oligonucleotide structure, the phosphate groups form the internucleotide backbone of the oligonucleotide. The normal linkage or backbone of RNA and DNA is a 3' to 5' phosphodiester linkage.

Examples of compounds useful in this invention include oligonucleotides containing modified backbones or non-natural internucleotide linkages. Possible modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and borano-phosphates having normal 3'-5' linkages, as well as their 2'-5'-linked analogs. These modified oligonucleotides may have inverted polarity, where one or more of the internucleotide linkages is a 3' to 3', 5' to 5', or 2' to 2' linkage. Oligonucleotides having inverted polarity may comprise a single 3' to 3' linkage at the 3'-most internucleotide linkage. Various salts, mixed salts and free acid forms of the modified and non-modified oligonucleotides are also included.

Preferred modified oligonucleotides may have backbones not including a phosphorus atom. These backbones may be formed by a short chain alkyl or cycloalkyl internucleotide linkage, or by one or more short chain heteroatomic or heterocyclic internucleotide linkages. These include oligonucleotides having morpholino linkages; siloxane backbones; sulfide, sulfoxide and sulfone backbones; formacetyl and thioformacetyl backbones; methylene formacetyl and thioformacetyl backbones; riboacetyl backbones; alkene-containing backbones; sulfamate backbones; methyleneimino and methylenehydrazino backbones; sulfonate and sulfonamide backbones; amide backbones; and others having mixed N, O, S, and $CH_2$ component parts.

In other oligonucleotide analogs, both the sugar and the internucleotide linkage of the nucleotides are replaced with novel groups. The base units are maintained to permit hybridization. One such oligomeric compound is a peptide nucleic acid, or "PNA." In PNA compounds, the sugar backbone of an oligonucleotide is replaced with an amide-containing backbone, such as an aminoethylglycine backbone.

Inhibitory compounds of the invention may be formed as composite structures of two or more oligonucleotides, modified oligonucleotides, oligonucleosides and/or oligonucleotide analogs as described above. Such compounds have also been referred to in the art as hybrids or gapmers.

A "coding sequence," or a sequence which "encodes" a particular protein, is a nucleic acid sequence (or a portion thereof) which is transcribed (in the case of DNA) or translated (in the case of mRNA) into a polypeptide in vitro or in vivo when placed under the control of appropriate regulatory sequences. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

For the purpose of describing the relative position of nucleotide sequences in a particular nucleic acid molecule throughout the instant application, such as when a particular nucleotide sequence is described as being situated "upstream," "downstream," "5'" or "3'" relative to another sequence, it is to be understood that it is the position of the sequences in the "sense" or "coding" strand of a DNA molecule that is being referred to, as is conventional in the art.

"Homology" refers to the percent of identity between at least two oligonucleotides or polypeptides. The percent identity between the sequences from one moiety to another can be determined by techniques known in the art. Homology can be determined by a direct comparison of the sequence information between two polypeptide molecules by aligning the sequence information and using readily available computer programs such as ALIGN, Dayhoff, M. O. (1978) in *Atlas of Protein Sequence and Structure* 5:Supp. 3, National Biomedical Research Foundation, Washington, D.C. Default parameters can be used for alignment. One alignment program is BLAST, used with default or manually set parameters. Details of these programs can be found, for example, on the website of the National Center for Biotechnology Information (NCBI).

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 90%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "functional homologue" or a "functional equivalent" of a given polypeptide includes molecules derived from the wild-type polypeptide sequence, as well as recombinantly-produced or chemically-synthesized polypeptides which function in a manner similar to the wild-type molecule to achieve a desired result. Thus, a functional homologue of Bcl-2 encompasses derivatives and analogues of those polypeptides—including any single or multiple amino acid additions, substitutions and/or deletions occurring internally or at the amino or carboxy termini thereof—so long as integration activity remains.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells.

By "vector" is meant any genetic element, such as a plasmid, phage, transposon, cosmid, chromosome, virus, virion, etc., which can transfer gene sequences into cells and which may or may not replicate in the host cells. Thus, the term includes cloning and expression vehicles, as well as viral vectors.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al., (1973) *Virology*, 52:456, Sambrook et al., (1989) *Molecular Cloning, a laboratory manual*, Cold Spring Harbor Laboratories, New York, Davis et al., (1986) *Basic Methods in Molecular Biology*, Elsevier, and Chu et al., (1981) *Gene* 13:197. Such techniques can be used to introduce one or more exogenous DNA moieties, such as a nucleotide integration vector and other nucleic acid molecules, into suitable host cells.

A "host cell" as used herein may be either a eukaryotic or a prokaryotic cell. In particular, a host cell could be a yeast cell, an insect cell, or a mammalian cell which has been transfected with an exogenous DNA sequence, and the progeny of that cell. It is understood that the progeny of a single parental cell may not necessarily be completely identical in morphology or in genomic or total DNA complement to the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription, and translation of a coding sequence in a recipient cell. Not all of these control sequences need to be present so long as the selected coding sequence is capable of being replicated, transcribed, and translated in an appropriate host cell.

"Operably linked" refers to an arrangement of elements wherein the components so described are configured to as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "prodrug" indicates a therapeutic agent that is prepared in an inactive form that is converted to an active form (drug) within the body or cells thereof by the action of endogenous enzymes or other chemicals and/or conditions.

The term "pharmaceutically acceptable salts" refers to physiologically and pharmaceutically acceptable salts of the compounds of the invention: i.e., salts that retain the desired biological activity of the parent compound without adding any undesired toxicological effects.

2. General Methods

Gene inhibition technologies are often used to modulate functions such as DNA replication or transcription, RNA translocation to the site of translation, RNA translation, RNA splicing, and catalytic activity conducted or aided by the RNA. In the present invention, the overall effect of such interference with the function of the target nucleic acid is modulation of the expression of Bcl-2. This is brought about by the interference of the single-stranded inhibitory oligonucleotides of the invention with Bcl-2 mRNA. The interference of the inhibitory oligonucleotides blocks proper function of the Bcl-2 mRNA, thus preventing proper expression. This interference is commonly referred to as "knockdown" of the target nucleic acid. This may result in the amelioration of disease symptoms or the curing of various diseases. In the context of this invention, "modulation" can mean either an increase or a decrease in the expression of a gene. In the instant invention, inhibition is a preferred form of modulation of gene expression, and mRNA is a preferred nucleic acid target.

Targeting inhibitory compounds to specific nucleic acids is generally a multistep process. First, a nucleic acid is identified that participates in a disease state. This nucleic acid is then sequenced. The nucleic acid may be, for example, a cellular gene or mRNA whose expression produces a product active in the disease, or in a nucleic acid molecule from infectious agent such as a virus, bacterium, or other infectious microbe. In this invention the target sequence is one encoding Bcl-2. A next step in the targeting process involves determining potential sites on the target nucleic acid molecule which are susceptible to interaction with an inhibitory oligonucleotide. This process also involves evaluating whether targeting one specific site will modulate the expression of a nucleic acid more effectively than targeting other specific sites.

In the present invention this targeting process may be conducted according to a variety of methods known in the art. Additionally, it may be conducted using the method outlined in U.S. Pat. No. 6,586,180, entitled Directed Antisense Libraries, which is incorporated herein in its entirety. That application discloses a procedure that allows the construction of directed antisense libraries.

These libraries contain all overlapping fragments spanning the entire length of the gene of interest. Transcription in vitro or in vivo of a DNA fragment produces an inhibitory RNA targeted to the site on the RNA transcript that is encoded by the DNA fragment. Transcription of the entire DNA fragment library produces all antisense RNA molecules targeting all positions on the RNA target. Expression of this library in mammalian cells therefore allows the identification of effective target sites on the nucleic acid for use in antisense-mediated gene inhibition.

The directed libraries generated above may be assayed for their ability to modulate the expression of target change in vivo in cultured cells. For such in vivo assays, the antisense library is transduced into a suitable cell line expressing the gene of interest. One of skill in the art may appreciate that transfection conditions may be chosen such that generally only one member of the library is taken up by each individual host cell. In this way each fragment of the gene of interest present in the library may be separately identified, characterized and isolated from other fragments of the gene of interest.

In one embodiment of the present invention, each member in the library is integrated into the chromosome of one cell at the same locus. This ensures that (1) only one member of the library is taken up by each individual host cell; (2) each member of the library will not be lost during cell division; (3) all members of the library will be expressed at the same level in the host cells. The result is a group of cells, each expressing a different inhibitory molecule targeted to a different site on the RNA transcript of the gene of interest. All target sites are present in the entire cell population produced. Using suitable detection methods, cell clones may be identified in which the expression of the target RNA has been reduced or eliminated. These clones possess an inhibitory oligonucleotide targeted to a site on the RNA transcript which allows effective modulation of the gene's activity. At this point, the plasmid, or a portion thereof encoding the inhibitory oligonucleotide may be recovered, and its sequence identified.

Once specific target sites have been identified, oligonucleotides are chosen which sufficiently complementary to the targets to obtain the desired effect. This can be accomplished by chemically synthesizing suitable oligonucleotides against the identified targets, delivering them exogenously to cells, and assaying the effect by standard methods used to measure gene expression. Alternatively, the oligonucleotides can be incorporated individually into a suitable vector and re-introduced into cells. Their effects are assayed using standard methods.

Thus, the invention includes inhibitory oligonucleotides directed to three different target regions and to subsequences of these regions found on nucleic acids encoding Bcl-2 to modulate the function of the nucleic acid. Each of these target regions contains many possible inhibitory oligonucleotides, each of which falls within the scope of this invention. The invention further includes specific inhibitory oligonucleotides identified from among the potential inhibitory oligonucleotides for each target sequence, which are presently preferred for the practice of this invention.

A first target region of the Bcl-2 nucleic acids (Region A) is found in SEQ ID NO: 19 and its sequence variant SEQ ID NO: 36. A subsequence of this first target region (SEQ ID NO: 15, and its corresponding sequence variant) provided a particularly high number of inhibitory oligonucleotides in the screening procedure. Region A is about 40 nucleobases in length, and the Region A subsequence represented by SEQ ID NO: 15 is about 30 nucleobases in length. Oligonucleotides complementary to a portion of the target region of Region A or to SEQ ID NO: 15 are inhibitory oligonucleotides which may modulate the expression of Bcl-2. These oligonucleotides may preferably be between from about 8 to about 30 bases in length, more preferably about 10 to about 26 nucleobases in length, and most preferably about 14 to about 20 nucleobases in length. Such oligonucleotides which are complementary to at least a portion of Region A or to at least a portion of SEQ ID NO: 15 include but are not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 14, SEQ ID NO: 22, SEQ ID NO: 23, SEQ ID NO: 24 and SEQ ID NO: 25, which are useful as inhibitory oligonucleotides in the practice of the invention. The invention further includes oligonucleotides comprising at least 8 contiguous nucleobases of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 14, SEQ ID NO: 22, SEQ ID NO: 23, SEQ ID NO: 24 and SEQ ID NO: 25, for use as inhibitory oligonucleotides.

A second target region of the Bcl-2 nucleic acids (Region B) is found in SEQ ID NO: 20 and its sequence variant SEQ ID NO: 37. A preferred subsequence of Region B for derivation of inhibitory oligonucleotides is SEQ ID NO: 16 and its corresponding sequence variant. Region B is about 62 nucleobases in length, and SEQ ID NO: 16 is about 14 nucleobases in length. Oligonucleotides complementary to at least a portion of the target region of Region B or to at least a portion of SEQ ID NO: 16 are inhibitory oligonucleotides which may modulate the expression of Bcl-2 and are typically about 10-26 nucleobases in length. These oligonucleotides may preferably be about 8 to about 14 nucleobases in length, more preferably about 10 to about 14 nucleobases in length, and most preferably about 12 to about 14 nucleobases in length. Such oligonucleotides which are complementary to Region B or to SEQ. ID. NO: 16 include, but are not limited to, SEQ ID NO: 8, SEQ ID NO: 9, SEQ ID NO: 26, SEQ ID NO: 27, SEQ ID NO: 28, SEQ ID NO: 29 and SEQ ID NO: 30, which are useful as inhibitory oligonucleotides in the practice of the invention. The invention further includes oligonucleotides comprising at least 8 contiguous nucleobases of SEQ ID NO: 8, SEQ ID NO: 9, SEQ ID NO: 26, SEQ ID NO: 27, SEQ ID NO: 28, SEQ ID NO: 29 and SEQ ID NO: 30 for use as inhibitory oligonucleotides.

A third target region of the Bcl-2 nucleic acids (Region C) is found in SEQ ID NO: 21. A preferred subsequence of SEQ ID NO: 21 for derivation of inhibitory oligonucleotides is SEQ ID NO: 17. Region C is about 23 nucleobases in length. SEQ ID NO: 17 is about 17 nucleobases in length. Oligonucleotides complementary to at least a portion of the target region of Region C or to at least a portion of SEQ ID NO: 17 are inhibitory oligonucleotides which may modulate the expression of Bcl-2 and are typically about 100-23 nucleobases in length. These oligonucleotides may preferably be between about 8 to about 17 nucleobases in length, more preferably about 10 to about 17 nucleobases in length, and most preferably about 12 to about 14 nucleobases in length. Such oligonucleotides which are complementary to Region C or to SEQ ID NO: 17 include, but are not limited to, SEQ ID NO: 10, SEQ ID NO: 11, SEQ ID NO: 12, SEQ ID NO: 13, SEQ ID NO: 31, SEQ ID NO: 32, SEQ ID NO: 33 and SEQ ID NO: 34, which are useful as inhibitory oligonucleotides in the practice of the invention. The invention further includes oligonucleotides comprising least 8 contiguous nucleobases of SEQ ID NO: 10, SEQ ID NO: 11, SEQ ID NO: 12, SEQ ID NO: 13, SEQ ID NO: 31, SEQ ID NO: 32, SEQ ID NO: 33 and SEQ ID NO: 34 for use as inhibitory oligonucleotides.

The oligonucleotides of the invention may be incorporated into pharmaceutical compositions. The oligonucleotides may additionally be used in methods to modulate the expression of Bcl-2 in a cell or tissue. Such methods may use the oligonucleotides alone, or they may use the pharmaceutical compositions of the invention.

Inhibitory oligonucleotide compounds are commonly used as research reagents and in diagnostics. Due to their ability to inhibit gene expression with specificity, such oligonucleotides are often used by those of ordinary skill to elucidate the function of particular genes. Inhibitory oligonucleotide compounds are also used to distinguish the functions of various members of a biological pathway.

The specificity and sensitivity of inhibitory oligonucleotide technology is also harnessed by those skilled in the art for therapeutic uses. One type of this technology is antisense oligonucleotides. Antisense oligonucleotides have been employed as therapeutic moieties in the treatment of disease states in animals and man. Other drugs, including ribozymes, have been safely and effectively administered to humans, and numerous clinical trials are presently underway. As useful therapeutic modalities, inhibitory oligonucleotides can be configured to be useful in treatment regimes for treatment of cells, tissues, and animals, especially humans.

The inhibitory compounds of this invention may be conveniently and routinely made through techniques such as solid phase synthesis. Equipment for such synthesis is sold by several vendors including, for example, Applied Biosystems, (Foster City, Calif.). Any other means for such synthesis known in the art may additionally or alteratively be employed. It is well known to use similar techniques to prepare oligonucleotides such as the phosphorothioates and alkylated derivatives.

The invention encompasses any pharmaceutically acceptable salts, esters, salts of such esters, or any other compounds which, upon administration to an organism such as a human, are capable of providing (directly or indirectly) the biologically active inhibitory oligonucleotides of the invention. Accordingly, for example, the disclosure is also drawn to prodrugs, and other bioequivalents. The compounds of the invention may also be admixed, encapsulated, conjugated or otherwise associated with other molecules, molecule structures or mixtures of compounds, as for example, liposomes, receptor targeted molecules, oral, topical and other formulations, for assisting in uptake, distribution and/or absorption.

The inhibitory compounds of the present invention can be used as diagnostics, therapeutics, prophylaxis, and as research reagents and kits. For therapeutics, an organism, such as a human, having a disease or disorder which can be treated by modulating the expression of Bcl-2 is treated by administering inhibitory compounds in accordance with this invention. The compounds of the invention can be utilized in pharmaceutical compositions by adding an effective amount of the inhibitory compound to a suitable pharmaceutically acceptable diluent or carrier. The inhibitory compounds and methods of the invention may also be useful to prevent or delay infection, inflammation, or tumor formation, for example.

The inhibitory compounds of the invention are useful for research and diagnostics because these compounds hybridize to nucleic acids encoding Bcl-2. Hybridization of the inhibitory oligonucleotides of the invention with a nucleic acid encoding Bcl-2 can be detected by means known in the art. Such means may include conjugating an enzyme to the oligonucleotides, radiolabeling the oligonucleotide, or using any other suitable detection means. Kits using such detection means for detecting the level of Bcl-2 present in a sample may also be prepared.

The pharmaceutical compositions of the present invention may be administered in a number of ways depending upon whether local or systemic treatment is desired and upon the area to be treated. Administration may be topical (including ophthalmic and to mucous membranes), pulmonary, e.g., by inhalation or insufflation of powders or aerosols, including by nebulizers; and tracheal, intranasal, epidermal, transdermal, oral, or parenteral. Parenteral administration includes intravenous, intraarterial, subcutaneous, intraperitoneal, or intramuscular injection or infusion, as well as intracranial (e.g., intrathecal or intraventricular) administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids, and powders. Conventional pharmaceutical carriers, aqueous bases, powder bases or oil bases, thickeners and the like may be necessary or desirable. Topical formulations include those in which the oligonucleotides of the invention are in admixture with a topical delivery agent such as lipids, liposomes, fatty acids, fatty acid esters, steroids, chelating agents and surfactants. Preferred lipids and liposomes may be neutral, negative, and cationic. Oligonucleotides of the invention may be encapsulated within liposomes or may form complexes thereto, such as cationic liposomes. Alternatively, oligonucleotides may be complexed to lipids, including cationic lipids.

3: EXAMPLES

Example 1

In a first example, an anti-Bcl-2 antisense oligonucleotide library was created using the methods of the invention outlined above. This antisense plasmid library contained nucleotides likely targeting every nucleotide position in the Bcl-2 RNA transcript. Nucleotide sequences which repressed the expression of Bcl-2 were isolated from this library by introducing the plasmid library into mammalian cells. The mammalian cells expressed the anti-Bcl-2 sequences upon the addition of an inducer, thus producing anti-Bcl-2 RNAs. Since inhibition of Bcl-2 is generally detrimental to cells, expression of the anti-Bcl-2 sequences was induced when the cells were ready to be sorted. In this example, tetracycline was used as the inducer. Other suitable systems of inducers and inducible promoters are known to those of skill in the art.

Following induction and expression of the anti-Bcl-2 sequences, Bcl-2 negative cells were sorted out from the others using a fluorescein-activated cell sorter. The anti-Bcl-2 nucleotide sequences from the Bcl-2 negative cells are then retrieved and sequenced. These anti-Bcl-2 sequences may be useful as therapeutic agents for diseases including cancer.

Example 2

The cell line A-2780R is derived from a human ovarian carcinoma and is known to express the Bcl-2 protein. When subcutaneously implanted into an athymic nude (immunodeficient) mouse host, A-2780R readily forms a progressively growing tumor mass. This provides a convenient in vivo model in which Bcl-2-active anticancer agents can be evaluated for therapeutic efficacy. In order to demonstrate the in vivo anticancer efficacy of a representative inhibitory oligonucleotide of the invention, athymic nude mice were subcutaneously implanted with A-2780R tumors. The tumor-bearing mice were then treated with G3139 (positive control: a Bcl-2 antisense oligonucleotide being developed by Genta, Inc.) or with SEQ ID NO: 32 (in DNA format). Tumor growth in these two treatment groups was compared to an untreated control group to determine therapeutic efficacy. Experimental details were as follows:

Female nude Balb/c mice (nu/nu), approximately 5 weeks old (Animal Technologies, Fremont, Calif.) were each implanted with $10^7$ A-2780R tumor cells by subcutaneous (SC) injection of 0.1 ml of inoculum into the right hind flank. The tumor cell inoculum was prepared in sterile DME/F-12 medium +10% fetal bovine serum, at a density of $1.0 \times 10^8$ cells/ml. When tumors were approximately 6 mm×6 mm in size (about 110 mg), the animals were group-matched into treatment and control groups, such that the mean tumor mass was normalized on a group-by-group basis (study day 1). Each group consisted of 4 animals. Mean body weight was about 20 gm at this time.

Solutions for injection of the phosphorothioate DNA oligonucleotides SEQ ID NO: 32 (Applied Biosystems, Salt Lake City, Utah) and G3139 (GENASENSE™, TriLink BioTechnologies, Inc., San Diego, Calif.) were prepared in phosphate buffered saline, pH 7.2 (PBS) at a final DNA concentration of 1.0 mg/ml. On study days 1, 2, and 3 each animal was administered a 0.2 ml volume of one of the solutions by IV injection into the lateral tail vein (200 µg of DNA or 10 mg DNA/Kg per dose). Untreated control animals received a sham injection of PBS only in the same manner as the oligonucleotide treatment groups.

Figure 1:
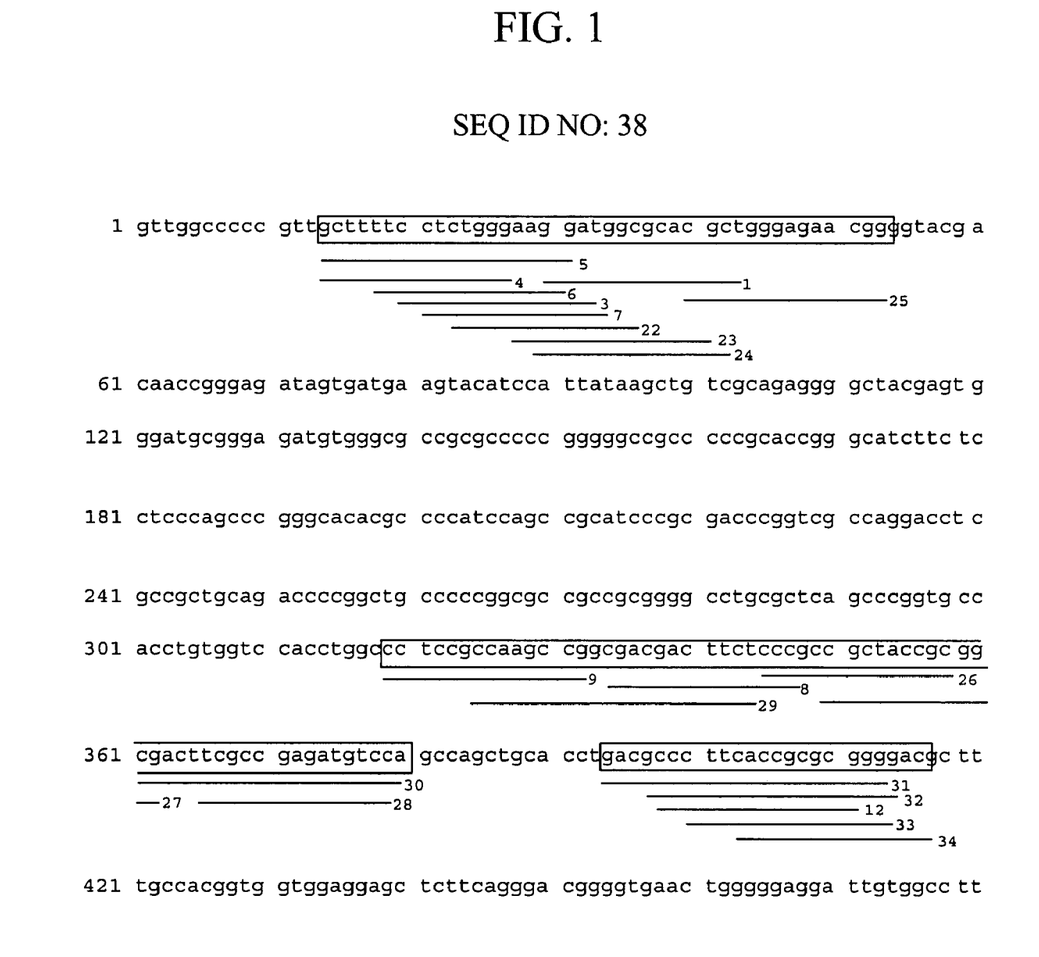
FIG. 1 is an anti-Bcl-2 antisense target map showing the inventive oligonucleotides and the corresponding region of a portion of the Bcl-2 cDNA from which they are derived (SEQ ID NO: 38).
Figure 2:
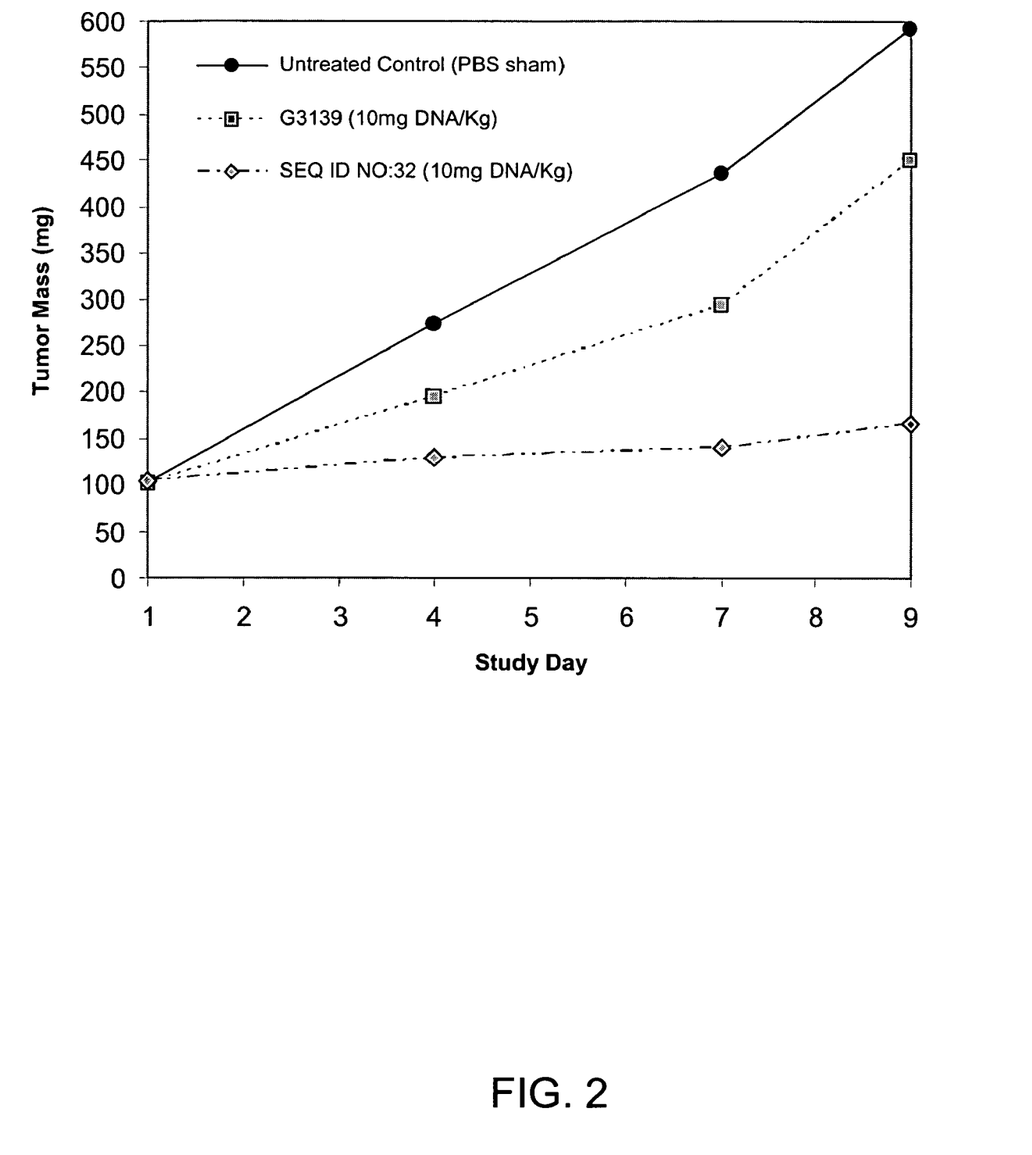
FIG. 2 shows the results of Example 2.

On study days 1, 4, 7 and 9 the animals were weighed. Tumor dimensions (length and width) were measured every other day and converted to tumor mass (mg) using the formula: Tumor Mass=$L^2 \times W/2$. The resulting tumor mass values were then averaged for each study group for each study day and were plotted against time. The results of the study as they relate to the effect of the oligonucleotides on tumor mass are shown in FIG. 2.

The tumor growth inhibitory activity of the two DNA oligonucleotides was summarized by calculating the percentage of tumor growth inhibition as compared to the untreated control group for the study day 4, 7 and 9 timepoints. Percent tumor growth inhibition was calculated using the formula: % Tumor Growth Inhibition=100−[(mean treated tumor wt./mean control tumor wt.)×100]. Tumor growth inhibitory activity is summarized in the following Table:

| Experimental Treatment | DNA Dose (mg/Kg) | % Tumor Growth Inhibition | | |
|---|---|---|---|---|
| | | Day 4 | Day 7 | Day 9 |
| Untreated Control | 0 | 0 | 0 | 0 |
| G3139 | 10 | 28.9 | 32.7 | 24.0 |
| SEQ ID NO: 32 | 10 | 52.5 | 67.9 | 72.0 |

Although both antisense Bcl-2 oligonucleotides were found to be inhibitory to the growth of A-2780R tumors, SEQ ID NO: 32 was approximately 2-fold more effective than the positive control (G3139) at each study timepoint. Treatment with SEQ ID NO: 32 resulted in a maximal tumor growth inhibition value of 72%, which occurred on study day 9. For animals treated with the positive control G3139, maximal tumor growth inhibition occurred on study day 7 and was found to be only 32.7%.

The effect of treatment on body weight was also evaluated. Weight loss in response to treatment is a general indicator of systemic toxicity. Percent change in body weight was calculated for each group at each study timepoint using the formula: % Change in Body Weight=[(mean body wt., day X−mean body wt., day 1)/mean body wt., day 1]×100. Both oligonucleotides were found to be well-tolerated by the animals through the duration of the study, as no weight loss occurred in any of the study groups.

Example 3

The cell line PC-3 is derived from a human prostate adenocarcinoma and is known to express the Bcl-2 protein. This cell line is therefore well suited for use in in vitro transfection studies for the evaluation of antisense Bcl-2 oligonucleotides. In order to demonstrate the in vitro cytotoxic or growth inhibitory activity of a representative inhibitory oligonucleotide of the invention against Bcl-2-expressing malignancies, PC-3 cells were transfected in vitro using SEQ ID NO: 5 and SEQ ID NO: 32 in DNA format. The antisense Bcl-2 DNA oligonucleotide G3139 was used as a positive control. Following transfection the effect on cell density was measured and cytotoxic or growth-inhibitory activity was determined by comparison to untreated control cells.

Experimental Details were as Follows:

The DNA oligonucleotides evaluated in the study were SEQ ID NO: 5 (Applied Biosystems, Salt Lake City, Utah), SEQ ID NO: 32 (Applied Biosystems, Salt Lake City, Utah), G3139 (MWG-Biotech, High Point, N.C.) and a DNA oligonucleotide derived from the Bcl-2 gene but outside of target Regions A, B and C.

The four antisense Bcl-2 DNA oligonucleotides were each initially diluted to a concentration of 4.0 μM using serum-free tissue culture medium (MEM/EBSS). Each oligonucleotide solution was then complexed to the transfection agent Lipofectamine 2000 (Invitrogen, life technologies) by addition of the DNA solutions to a separate set of Lipofectamine 2000 solutions (also prepared in serum-free tissue culture medium), such that the coupling ratio of DNA (in μg): Lipofectamine 2000 (in μl) was 1:2.5. A separate Lipofectamine 2000 control solution was also prepared, which contained Lipofectamine 2000 at an equivalent concentration, diluted in serum-free medium without DNA (the Lipofectamine control). In the same manner a second set of DNA solutions was prepared in serum-free medium, but which did not contain the Lipofectamine 2000 transfection agent (DNA control). The resulting solutions were mixed and incubated at room temperature for 20 min. to allow the complexation interaction to reach equilibrium. Each of the resulting nine solutions was serially diluted in two-fold steps using serum-free tissue culture medium. A suspension of PC-3 cells (American Type Culture Collection, Manassas, Va.) was prepared at a density of $1 \times 10^6$ cells/ml in tissue culture medium (MEM/EBSS) supplemented with 20% fetal bovine serum. Each of the DNA-Lipofectamine 2000 complex solutions, uncomplexed DNA control solutions and Lipofectamine 2000 control solutions (50 μl) were placed into the wells of a 96-well assay plate, followed by 50 μl of PC-3 cell suspension (50,000 cells). Cell control wells contained 50,000 PC-3 cells in 100 μl of tissue culture medium supplemented with 10% fetal bovine serum. All wells were prepared in duplicate. The assay plates were then incubated at 37° C. in an atmosphere containing 5% $CO_2$ (95% air) and humidity for 72 hours.

Figure 3:
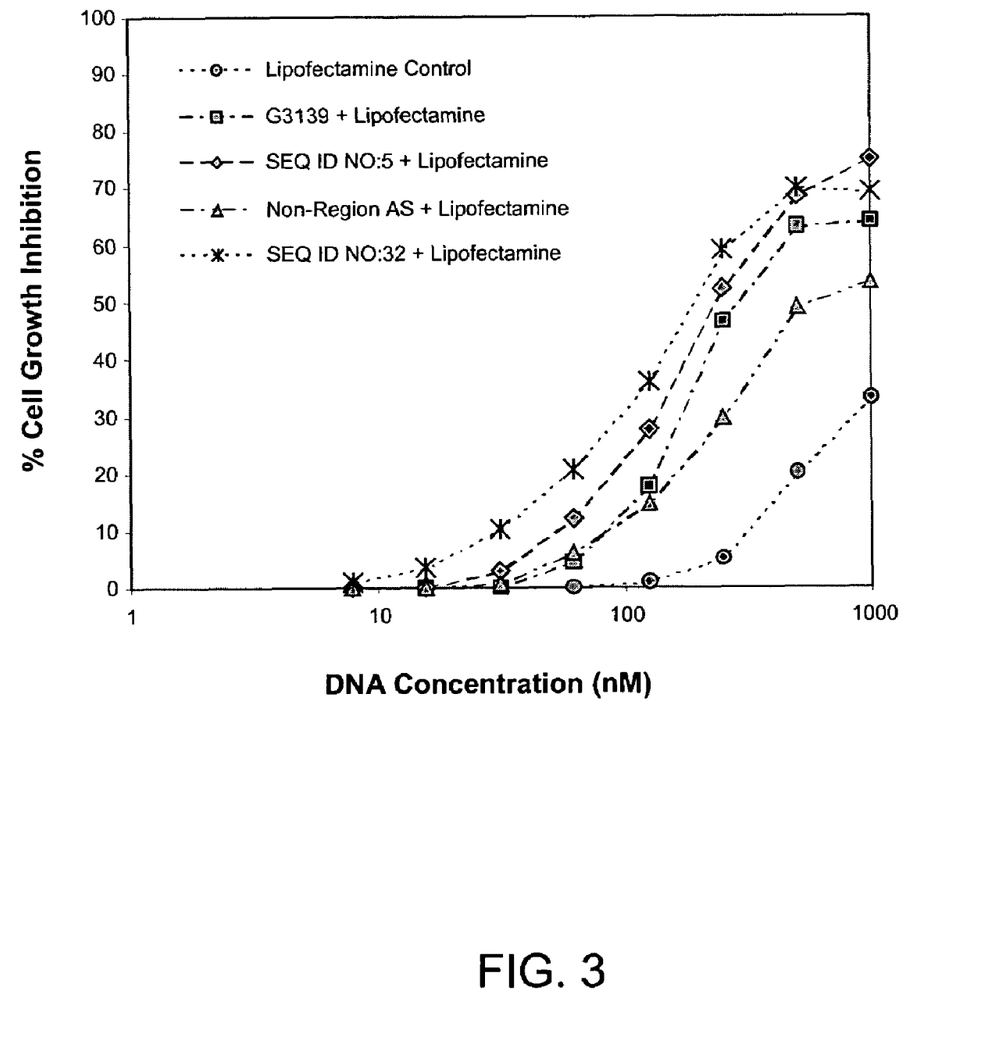
FIG. 3 shows the results of Example 3.

Following the 72 hour incubation, 20 μl of MTS/PES solution (Promega CellTiter 96 AQ One Solution Cell Proliferation Assay, No. G-3580) was added to each well of the plates. The assay plates were incubated for an additional 2 hours at 37° C. as described above. Using a 96-well microplate reader the absorbance of each well was measured at 490 nm. The instrument was zeroed using wells containing 100 μl of tissue culture medium supplemented with 10% fetal bovine serum and 20 μl of MTS/PES solution. The mean absorbance value was calculated for each duplicate pair of wells, and the resulting values were then used to calculate % growth inhibition using the formula: % Growth Inhibition=(1−[Abs. Transfected Test Group/Abs. Cell Control])×100. Dose response curves were plotted using a linear y-axis scale for % cell growth inhibition and a logarithmic x-axis scale for DNA concentration. The cell growth inhibitory activity was compared between each transfection group by determining the 50% inhibitory concentration ($IC_{50}$) value for each group. The $IC_{50}$ value is defined as the DNA concentration which resulted in the inhibition of growth or death of 50% of the cells as compared to the untreated control (cell control). The results are shown in FIG. 3

The corresponding $IC_{50}$ values for each transfection group are shown in the following Table:

| Experimental Treatment | $IC_{50}$ (DNA Conc.) |
|---|---|
| Lipofectamine Alone (control) | >1000 nM equiv. |
| G3139 DNA + Lipofectamine | 280 nM |
| SEQ ID NO: 5 + Lipofectamine | 233 nM |
| SEQ ID NO: 32 + Lipofectamine | 184 nM |
| Non-Region A, B, C oligo + Lipofectamine | 503 nM |

When complexed to the Lipofectamine 2000 transfection agent, all four antisense Bcl-2 DNA oligonucleotides resulted in inhibition of PC-3 cell growth at 72 hours following initiation of transfection. SEQ ID NO: 32 (Region C) was found to be the most active, having an $IC_{50}$ value of 184 nM, which was 1.52-fold more active than the G3139 positive control (Region A, $IC_{50}$=280 µM). The $IC_{50}$ value for SEQ ID NO: 5 (Region A) also indicated a high level of inhibitory activity. The non-Region A, B, C oligonucleotide, although active, was substantially less inhibitory than the oligonucleotides derived from the target regions of the invention. The Lipofectamine 2000 control was only minimally toxic to the cells at the highest concentration. Cells treated with DNA alone (in the absence of Lipofectamine 2000 transfection agent) showed little or no inhibition of growth.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. An isolated oligonucleotide from about 10 to about 30 nucleobases in length comprising a sequence of at least 8 contiguous nucleobases of SEQ ID NO: 10, SEQ ID NO: 11, SEQ ID NO: 12, SEQ ID NO: 13, SEQ ID NO: 31, SEQ ID NO: 32, SEQ ID NO: 33, SEQ ID NO: 34 or any of the foregoing SEQ ID NOs., wherein U is substituted for T, wherein the isolated oligonucleotide is at least about 95% homologous over its full length to SEQ ID NO: 10, SEQ ID NO: 11, SEQ ID NO: 12, SEQ ID NO: 13, SEQ ID NO: 31, SEQ ID NO: 32, SEQ ID NO: 33, SEQ ID NO: 34 or any of the foregoing SEQ ID NOs., wherein U is substituted for T.

2. The oligonucleotide of claim 1 which is specifically hubridizable to SEQ ID NO: 17, SEQ ID NO: 21, or any of the foregoing SEQ ID NOs., wherein U is substituted for T.

3. The oligonucleotide of claim 1 which is SEQ ID NO: 10, SEQ ID NO: 11, SEQ ID NO: 12, SEQ ID NO: 13, SEQ ID NO: 31, SEQ ID NO: 32, SEQ ID NO: 33, SEQ ID NO: 34 or any of the foregoing SEQ ID NOs., wherein U is substituted for T.

4. The oligonucleotide of claim 1 which is about 10-23 nucleobases in length.

5. The oligonucleotide of claim 1 which is an RNA oligonucleotide.

6. The oligonucleotide of claim 1 which comprises a non-naturally occurring nucleobase, sugar or internucleotide linkage.

7. The oligonucleotide of claim 6 which comprises a phosphorothioate internucleotide linkage.

8. A composition comprising the oligonucleotide of claim 1 and a pharmaceutically acceptable carrier, diluent or adjuvant.

* * * * *